(12) United States Patent
Elsohly et al.

(10) Patent No.: US 6,730,519 B2
(45) Date of Patent: May 4, 2004

(54) METHOD OF PREPARING DELTA-9-TETRAHYDROCANNABINOL

(75) Inventors: Mahmoud A. Elsohly, Oxford, MS (US); Samir A. Ross, Oxford, MS (US)

(73) Assignee: The University of Mississippi, University, MS (US)

( * ) Notice: Subject to any disclaimer, the term of this patent is extended or adjusted under 35 U.S.C. 154(b) by 141 days.

(21) Appl. No.: 10/006,264

(22) Filed: Dec. 4, 2001

(65) Prior Publication Data

US 2002/0086438 A1 Jul. 4, 2002

Related U.S. Application Data

(63) Continuation-in-part of application No. 09/178,962, filed on Oct. 26, 1998, now Pat. No. 6,365,416.
(51) Int. Cl.[7] .................................................. G01N 30/02
(52) U.S. Cl. ...................... 436/161; 436/93; 436/177; 436/178; 436/901; 514/454; 549/388
(58) Field of Search .................................. 436/177, 178, 436/161, 93, 901; 514/454; 549/388

(56) References Cited

FOREIGN PATENT DOCUMENTS

WO    WO-02/32420 A1  *  4/2002

OTHER PUBLICATIONS

Mechoulam et al., Fortschr. Chem. Org. NatStoffe (1967), vol. 25, pp. 175–213.*
Verwey et al., Pharm. Weekblad (1972), vol. 107, pp. 415–416.*

* cited by examiner

*Primary Examiner*—Jan Ludlow
(74) *Attorney, Agent, or Firm*—Greenberg Traurig LLP; Eugene C. Rzucidlo

(57) ABSTRACT

A method for the isolation of delta-9-tetrahydrocannibinol (THC) from, Cannabis plant material, wherein delta-9-THC Acid and THC are separately obtained including the steps of extracting the Cannabis plant material, chelating delta-9-THC acid on alumina solid support from cannabis extracts rich in the acid washing of non-acid components of the extract with organic solvents and eluting of the delta-9-THC acid with strong polar solvents.

5 Claims, No Drawings

METHOD OF PREPARING DELTA-9-TETRAHYDROCANNABINOL

CROSS-REFERENCE TO RELATED APPLICATIONS

This application claims priority from, and is a continuation-in-part of, Elsohly et al., "Method of Preparing Delta-9 Tetrahydrocannabinol," U.S. patent application Ser. No. 09/178,962, filed Oct. 26, 1998, now U.S. Pat. No. 6,365,416 herein incorporated by reference.

GOVERNMENT SUPPORT

Funding for this continuation-in-part application has been provided by a grant from NIDA, Grant Number SBIR No. N44-DA-0-7706 for "Development of an Economical Supply of Delta-9-THC". The government may have certain rights in this particular continuation-in-part invention.

BACKGROUND OF THE INVENTION

Delta-9-tetrahydrocannabinol (THC, also known as dronabinol) is the main biologically active component in the Cannabis plant which has been approved by the Food and Drug Administration (FDA) for the control of nausea and vomiting associated with chemotherapy and, more recently, for appetite stimulation of AIDS patients suffering from the wasting syndrome. The drug, however, shows other biological activities which lend themselves to possible therapeutic applications, such as in the treatment of glaucoma (1), migraine headaches (2, 3), spasticity (4), anxiety (5), and as an analgesic (4). It is because of these-promising biological activities of THC that marijuana has been brought into a public debate relative to its medicinal value. The balance between medicinal use of a drug and the abuse potential is a delicate balance. One of the main points brought by the medicinal marijuana proponents is the fact that the currently available soft gelatin capsule formulation is very expensive and lacks consistency in its effects. The latter point could be explained based on the fact that oral THC has erratic absorption from the gastrointestinal tract, is subject to the first-pass effect resulting in heavy metabolism with production of high levels of 11-OH-THC, and undesirable side effects. Another THC formulation which is currently under development is a pro-drug consisting of THC hemisuccinate formulated in a suppository base (6). This formulation appears to overcome the problems associated with the oral preparation and has been shown to produce consistent bioavailability in animal studies (7). Preliminary clinical investigations show promise for this formulation (8, 9, 10). It is anticipated that other THC formulations will be forthcoming in light of the current interest in the therapeutic activities of cannabis.

Regardless of which formulation is to be used for THC or a pro-drug thereof, a source for the raw material is critical. The currently-approved capsule formulation is prepared from synthetic THC which is extremely expensive to produce. It is thought that should an economic process be developed for isolation of THC from the natural material (cannabis), then the cost of the raw material could be brought down significantly, making it possible to develop such formulations at a reasonable cost to the public. The consequence of this would be the availability of alternative therapies involving THC (or a prodrug thereof) which would help in suppressing the public outcry for approval of marijuana as a medicine.

Several investigations have been carried out over the years to isolate THC from the plant material, mostly to determine its chemical structure or to investigate the phytochemistry of the plant. In 1942, Wollner, et al., (11) reported the isolation of tetrahydrocannabinol from cannabis extract "red oil". Red oil was prepared by extraction of the plant material with ether, followed by distillation of the concentrated extract at room pressure followed by redistillation under reduced pressure (15–50 mm Hg). The oil was acetylated with acetic anhydride, and the acetylated product was subjected to fractional distillation in vacuo. Six fractions were collected. The head and tail fractions were removed. The remaining four fractions which represent the principal fractions (fractions 2, 3, 4, and 5) were combined and passed over silica gel column in benzene and then passed over activated alumina in carbon tetrachloride solution. The product was hydrolyzed by acid, alkali, or ammonia in alcoholic solution. The authors reported that the deacetylated product has, in each case, a different physiological potency than the acetate. All fractions were not pure compounds.

DeRopp, in 1960 (12), described the isolation of THC from the flowering tops of *Cannabis sativa*. His method involved adsorption chromatography of the methanolic extract of cannabis followed by partition chromatography on Celite using N,N-dimethyl formamide/cychlohexane mixture and high vacuum distillation. The purity of THC was based on paper chromatographic evidence.

The first isolation of the naturally occurring THC in its pure form was reported by Gaoni and Mechoulam in 1964 (13). THC was isolated from the hexane extract of hashish by repeated column chromatography on florisil and alumina. Further purification was carried out by the preparation of the crystalline 3,5-dinitrophenylurethane of THC followed by mild basic hydrolysis to get the pure THC. The purity of THC was proven by thin layer chromatography (TLC) and spectroscopic analysis (IR and NMR).

Korte, et al., in 1965 (14) reported the isolation of THC from the crude extracts of the female inflorescence of *Cannabis sativa indica* and *Cannibis sativa non indica*. The crude extracts were chromatographed over activated alumina in order to remove the coloring impurities like carotinoids, chlorophylls and xanthophylls. All the cannabinolic fractions were combined and concentrated to give a brownish-red oil. The oil was further purified by a counter-current distribution method to get THC which was proved to be identical with that described by Gaoni and Mechoulam (13).

In 1967, Mechoulam and Gaoni (15) reported the isolation of THC from the acidic fraction of the hexane extract of hashish. The hexane extract of hashish was separated into acidic and neutral fractions. The acidic fraction was chromatographed on florisil or acid washed alumina. The column was eluted with pentane-ether mixtures in a manner of increasing polarities. THC was eluted with 15% ether in pentane. Repeated chromatography was carried out by the preparation of crystalline derivative (3,5-dinitrophenylurethane THC, m.p., 115–116° C.) followed by hydrolysis.

In 1972, Verwey and Witte (16) reported a method for the preparation of THC by isolation of THC acid from hashish. The hexane extract was shaken with 2% NaOH solution as well as 2% sodium sulphite in an extraction funnel. The alkaline layer was rendered acidic with $H_2SO_4$ (pH<2), thus precipitating the cannabinoid acids. The oily layer as well as the oily deposits on the wall were extracted with ether. The acid-base extraction process was repeated. THC was obtained from the impure acids by heating the ether solution containing the acids on a sand bath with a temperature of 300° C. The ether being evaporated, the evaporating dish was for a moment kept on the sand bath, in this way causing decarboxylation of THC acid. The THC was cleaned by preparative TLC.

In summary, for isolation of THC and other cannabinoid constituents, generally the alcoholic or the petroleum ether or benzene or hexane extract of the plant is separated into neutral and acidic fractions. These fractions are further purified by repeated column chromatography and counter-current distribution or a combination of these methods. Various adsorbents have been used in column chromatography, especially silica gel, silicic acid, silicic acid-silver nitrate, florisil, acid washed alumina, and acid washed alumina-silver nitrate. Most of the above-discussed methods were used for the preparation of a small amount of THC and not for large-scale production.

If THC is to be prepared in large-scale (kilogram) quantities, an efficient and economic method is needed. Such a method would require an efficient isolation procedure.

SUMMARY OF THE INVENTION

The present invention relates to improvements for the obtaining of THC and THC-acid from Cannabis plant material. Simple, high yielding steps are developed which reduce the cost of preparation of THC several fold over the synthetic route.

The present invention relates to improvements in a process which comprises a process wherein Cannabis plant material is extracted with a non-polar organic solvent to provide an extract containing THC and the extract is subjected to fractional distillation under reduced pressure to provide a distillation fraction (distillate) having a high content of THC. The process further comprises subjecting the extract from the plant material to column chromatography prior to fractional distillation. A still further aspect of the process comprises subjecting the distillate from the fractional distillation to column chromatography. Additionally, the invention includes the use of high pressure liquid chromatography (HPLC) in the purification of the extract from the plant material.

The improvement of the present invention relates to a process in which the THC content of cannabis extract or a distillation residue is increased by treating the extract or residue with polar, water miscible organic solvents in admixture with water to form a precipitate and concentrating the filtrate to give a concentrated extract.

A further improvement is a process of chelating THC acid contained in a cannabis extract containing the acid on alumina, washing off the nonacid components with the moderately polar solvents and eluting the alumina with strong polar solvents to provide the separated THC-acid.

DETAILED DESCRIPTION OF THE INVENTION

The present invention provides an improvement to a procedure for providing an efficient and economic method for isolating THC from Cannabis plant material. The plant material is extracted with a non-polar organic solvent. Useful solvents include lower alkanes, such as, for example, hexane, heptane or iso-octane. The extract containing THC, after solvent removal, is subjected to fractional distillation at reduced pressure and a second distillate is collected. In one embodiment of the present invention, the first distillate is again subjected to fractional distillation at reduced pressure and a second distillate is collected. The second distillate has a THC content of greater than 90% by wt.

In another embodiment of the invention, which is improved by applicants, the crude extract from the plant material is first subjected to column chromatography. One possible method by which the material can be placed on the column is by mixing the extract residue in an organic solvent with a portion of the column packing material and transferring the dried slurry onto the top of a packed column. Direct application of the extract residue in the initial elution solvent (minimum volume) directly to the top of the packed column is also possible. The column is eluted with an organic solvent in a manner such that the column is eluted with a solvent or a solvent mixture with progressively increasing polarity. The fraction or fractions containing the major portion of THC from the column elution is subjected to fractional distillation at reduced pressure. Distillate is collected in the substantially constant boiling temperature range and this distillate was found to contain greater than 90% by weight THC. THC with purity of greater than 95%, preferably greater than 98% can be obtained by further purification of the distillate from fractional distillation by column chromatography or by normal or reversed phase HPLC.

The column chromatography can be carried out using any known packing material including, for example, silica or alumina for normal phase operation or $C_{18}$ or $C_8$ bonded phase silica for reversed phase operation. Elution of the normal phase chromatography column is carried out with solvents having an increasing polarity. Non-polar solvents include the lower straight chain and branched chain alkanes, including, for example, pentane, hexane, isooctane and petroleum ether. More polar solvents include various organic ethers, alcohols, esters or ketones, including, for example dialkyl ethers, lower alkyl acetates, lower dialkyl ketones and lower alkanols. Illustrative polar solvents include, for example, acetone, ethylacetate, diethylether and isopropyl alcohol. The ratio of non-polar solvent to polar solvent can vary between 100:0 to 80:20.

Elution chromatography under the reversed phase conditions is carried out with solvents having decreasing polarities. These solvents include water or acidic buffer as the polar portion and lower alkanol (such as methanol, ethanol and isopropanol) or acetonitirle as the less polar portion, in mixtures ranging from 50:50 to 0:100 aqueous to organic. The chromatographic process can also be carried out under HPLC conditions in much the same way as described above under either normal or reversed phase operation using a preparative scale column.

Flash distillation is carried out under reduced pressure, i.e. under vacuum at pressures below 1 mm Hg, preferably close to 0.1 mm Hg.

Improving the Delta-9-THC Content of the Cannabis Extracts Prior to Chromatography and/or Fractional Distillation The concentration of delta-9-THC in the initial cannabis extract is a function of the potency (% THC) of the starting plant material. For example, cannabis plant material with THC content of approximately 3% will produce a hexane extract of approximately 35% THC in the first extract and less than 20% in the second extract which might necessitate keeping the first and second extracts separate for further processing. Cannabis biomass of 4% will produce a first hexane extract of approximately 40% THC and a second extract of slightly over 20% THC, while extracts of 5–7% THC plant material will produce a first hexane extract of 45–55% THC with a second extract of approximately 25% THC.

Processing of cannabis extracts of less than 40% THC (whether it be a first extract of a low potency plant material or the second extract of almost any plant material) would be made much more economic if one could pre-treat such extract in a simple step that would result in increasing the THC content to approximately 40% or more. It has been discovered that treatment of "low THC" extracts with one of a selection of polar, water missible solvents (such as, for example, lower alkyl alcohols, dialkyl ketones, such as, for example acetone or methylethyl) or acetonitrile in combination with water in various ratios would result in precipitation of significant amount of residue containing small percentage of THC, leaving behind (in solution) the main bulk of THC. A simple filtration step results in removal of the unwanted residue, and evaporation of the solvent of the filtrate results in a concentrated extract with much lower weight than the starting extract and much higher THC content. The resulting extract could then be processed as usual. Furthermore, the residue left from fractional distillation of cannabis extracts is usually of low THC content. This material could be reprocessed in the same manner as discussed above, making the overall process more economical.

Chelation of $\Delta^9$-THC-Acid A on Alumina Stationary Phase

Delta-9-THC (1) exists in the fresh cannabis plant material as its precursor $\Delta^9$-THC-acid A (2) almost exclusively.

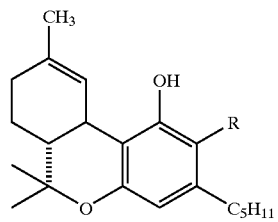

1 R = H = $\Delta^9$-THC
2 R = COOH = $\Delta^9$-THC-acid A

During the drying and extraction processes variable amounts of the precursor acid 2 is decarboxylated to 1 with the resulting extracts containing a mixture of 1 and 2, in a ratio that depends on the drying and extraction conditions. Under mild conditions of drying of the plant material (40°–50°) and mild temperature of evaporation of the extraction solvent, the main component of extract is the acid precursor 2.

The improvement of this invention is, therefore, directed especially to extracts prepared under conditions which preserve the $\Delta^9$-THC-acid A and minimize decarboxylation to $\Delta^9$-THC.

Treatment of a solution of an extract with alumina allows the strong binding (chelation) of the acid to the exclusion of other components (neutral cannabinoids and the non-cannabinoid components such as terpenes, hydrocarbons, sterols, etc.). The alumina could then be washed (eluted) with non-polar to moderately polar solvents to remove unwanted components followed by elution of $\Delta^9$-THC-acid A using strong solvents such as, for example, methanol with varying amounts of acetic acid.

The eluted acid could then be subjected to fractional distillation to give $\Delta^9$-THC in a relatively pure form (>80% chromatographical purity) with a final chromatographic step to remove minor impurities. Alternatively, the eluted acid could be further purified from other similar cannabinoid acids, with the fractional distillation step used at the end to generate $\Delta^9$-THC in a pure form.

The alumina chelation, therefore, offers an alternative clean-up step which has the advantage of providing the THC-acid A in relatively pure form in a simple adsorption (filtration) step. This could be especially useful if one desires the separation of the pure acid A for biological evaluation without losing the ability to generate $\Delta^9$-THC from the acid by a simple fractional distillation step.

It is to be noted that all three types of alumina solid supports could be used for this process (basic, neutral, and acidic), although basic alumina is preferred.

It will be understood by those skilled in the art that various modifications and substitutions may be made to the invention as described above without departing from the spirit and scope of the invention. Accordingly, it is understood that the present invention has been described by way of illustration and not limitation.

EXAMPLE NO. 1

Extraction 200 g of the air-dried and powdered buds (7.82% THC) and 270 g of the air-dried and powdered buds (6.61% THC) were mixed and extracted by maceration at room temperature with hexane for 24 hours (2.2 L Hexane×4). The hexane extracts were combined and evaporated under vacuo to give 76.5 g (16.3% extractives).

Column Chromatography 56 g of the hexane extract (40% THC) was mixed with 100 g silica gel (silica gel 60, E. Merck) and 50 ml hexane. The dried slurry was transferred onto the top of a silica gel column (850 g silica gel 60, dimensions: 10×60 cm). Elution was carried out with petroleum ether and ether in manner of increasing polarities. Twelve fractions were collected and TLC screened. Identical fractions were pooled together. The fraction eluted with Pet.ether-ether (9:1) was evaporated to give 37.3 g of residue which showed THC content of 55.87% using gas chromatography (GC) analysis. This fraction contained the majority of THC (93%) in the material applied onto the column.

Fractional Distillation

A portion (7.1 g) of the collected fraction was subjected to fractional distillation under vacuum (between 0.08–0.1 mmHg) to get two major fractions, one collected between 170–175° C. (2.34 g @90% THC) and one between 175–180° C. (1.32 g @88.2% THC).

EXAMPLE NO. 2

Extraction

The air-dried and powdered buds (380 g, 2.20% THC) were extracted with hexane by maceration at room temperature for 24 hours (1.8 L hexane×3). The total weight of the hexane extracts was 29.1 g (7.7% extractives). The % of THC in the hexane extract was 28.76%.

Column Chromatography

The hexane extract (29.1 g) was mixed with 100 g of silica gel (silica gel 60, E. Merck) and 50 ml hexane. The dried slurry was transferred on to the top of silica gel column (850 g silica gel 60, Dimensions: 10×60 cm). Elution was carried out with petroleum ether-ether mixtures in a manner of increasing polarities. Nine fractions were collected and TLC screened. Identical fractions were pooled together to give 4 fractions. The fraction collected with petroleum either-ether (9:1) was evaporated to yield 13.3 g of residue. GC analysis of this fraction showed a concentration of THC of 58.98%, again representing >93% recovery of all THC in the material applied to the column.

Fractional Distillation

A portion (7.3 g) of the fraction collected above was subjected to fractional distillation at vacuum (0.08–0.1. mmHg). The major fraction (3.738 g) was collected between 172–180° C. and was found to contain 89% THC by weight.

EXAMPLE NO. 3

One kg of the fine powdered marijuana plant material [average % of THC was about 5.21%] was macerated with 6 L hexanes (Hexanes GR from EM Sciences) in a percolator (9" in diameter from the top and 20 " long, cone shaped) for 24 hours at room temperature and filtered. The macerate was reextracted with 5 L hexanes for another 24 hours. The hexane extracts were combined and evaporated under reduced pressure at low temperature to give 110.7 g residue (11.07% extractives). The % of THC in the hexane extract was 41.21%.

Column Chromatography

The hexane extract (110.7 g) was mixed with 150 g silica gel (silica gel 60, Art.# 9385-3) and 50 ml hexane. The air dried slurry was transferred to the top of a silica gel column (800 g silica gel 60, particle size 0.04–0.063 mm, from EM Science, Art. # 9385-3). The column was eluted with hexane: ether mixtures in a manner of increasing polarities. Fractions were collected and TLC screened (analytical silica gel plates, developing system: Hexane: Ether (80:20), Visualizing agent: Fast blue). The fractions collected with hexane (3 L.) and hexane-ether (95:5, 2 L.) were discarded. The following fractions collected with hexane-ether (95:5, 3 L.) and hexane-ether (9:1, 5 L.) were combined and evaporated to yield 77.2 g of residue. GC analysis of the residue showed THC concentration to be 54.74%.

Fractional Distillation

A portion (30.5 g) of the residue collected above was subjected to fractional distillation under reduced pressure (0.1–0.15 mm/Hg). The temperature was slowly raised to 125° C. and the materials collected were kept separate. The temperature was then raised between 140–160° C. where the major fraction was collected (14 g). GC analysis showed >96% THC.

EXAMPLE NO. 4

One kg of the fine powdered marijuana plant material [average % of THC is 4.42] was macerated with 6 L hexanes and extracted by the same procedure followed in Example 3 to yield 105.8 g residue (10.58% extractives). The % of THC in the hexane extract was 40.35% by GC analysis.

Direct Fractional Distillation Of The Hexane Extract

A portion (23.0 g) of the hexane extract was subjected to fractional distillation under reduced pressure (vacuum, 0.1–0.2 mm/Hg). The temperature was raised slowly to 160° C. where a small amount of material (<1 g) was collected and left separate. The major fraction (10.1 g) was collected between 170 and 180° C. GC analysis of this fraction showed 72.66% THC concentration.

A second portion (25.0 g) of the hexane extract was subjected to fractional distillation under similar conditions as the first portion. The major fraction collected between 170–180° C. weighed 11.6 g and had a THC concentration of 73.62%.

A third portion (25.0 g) of the hexane extract was subjected to fractional distillation under similar conditions to the previous portions. The major fraction containing THC weighed 10.2 g and had a THC concentration of 73.72%.

The three major fractions obtained from the above three distillations were combined and analyzed. The analysis showed the concentration of THC to be 70.31%. The mixture (28.9 g) was subjected to fractional distillation, again under similar conditions. The temperature was raised slowly to 135° C. under vacuum (0.1–0.15 mmHg) and the fractions collected were kept aside. The major THC containing fraction was collected at 140–160° C. and 0.05–0.06 mm/Hg. The fraction weight was 18.4 g and the THC content was 92.15%.

EXAMPLE NO. 5

A portion (0.8 g) of the pure THC obtained in Example No. 3 (% of THC was about 96%) was mixed with one gram silica gel (silica gel 60) and one ml hexane. The dried slurry was transferred on to the top of a silica gel column (12 g silica gel 60, Dimensions: 1×50 cm). Elution was carried out with hexane:ether mixtures in a manner of increasing polarities. Six fractions were collected and screened using TLC. Fraction Nos. 3–5 (hexane:ether 98:2) were combined and yielded 0.63 g of residue (% of THC was 98%).

EXAMPLE NO. 6

One gram of the THC prepared in Example No. 4 purity was about 92%) was mixed with one gram of silica gel (silica gel 60) and one ml hexane. The dried slurry was transferred on to the top of a silica gel column (13 g silica gel 60, dimensions: 1×50 cm). Elution was carried out under similar conditions as under Example 5. Fraction nos. 3–5 yielded 0.78 g of residue (% of THC was 98%).

EXAMPLE NO. 7

1000 g of the air-dried and powdered Cannabis (buds % of THC by GLC analysis was 6.49%) were extracted by maceration at room temperature for 24 hours (5 L×3, Lot. No. 970424). The hexane extracts were combined and evaporated under vacuo to give 97 g residue.

67 g of the hexane extract was dissolved in 200 ml isooctane (Lot. No. 904038) and the solution was transferred onto the top of a silica gel column (280 g silica gel, 40 Mm particle size, dimensions of column: 10×60 cm). The column was eluted with iso-octane:methyl-t-butyl ether mixture 8:2 (3 L, fraction 1) and then washed with methanol (1 L, fraction 2). GLC analysis of fraction 1 (53 g) showed a concentration of THC of 55.56%.

Fractional Distillation

Fraction 1 (53 g) was subjected to fractional distillation at vacuum 0.1–0.6 mm/Hg. The major fraction (20.0 g) was collected between 160–170° C. and was found to contain 94% THC by weight.

Purification Of THC By HPLC 10 g of the major fraction (purity about 94%) was purified on HPLC (water Delta prep 4000) connected to a Waters 486 Tunable absorbance detector and using column Prep PAK500/silica. The eluent was iso-octane:methyl-t-butyl ether mixture (98:2). The flow rate was programmed to be 10 ml/minute for 10 minutes, 25 ml/minute for 60 minutes and finally 50 ml/minute for 200 minutes.

The results are summarized in the following table:

| FRACTIONS | TIME (minutes) | VOLUME (ML) | WEIGHT (G) | ANALYSIS FOR THC |
|---|---|---|---|---|
| 1 | 22–48 | 600 | trace | |
| 2 | 67–72 | 300 | 0.3 g | |
| 3 | 72–74 | 100 | 0.9 g | |
| 4 | 74–81 | 450 | 2.7 g | 96.6% |
| 5 | 81–97 | 800 | 4.0 g | 99.0% |
| 6 | 97–100 | 1200 | 1.9 g | 97.5% |

Purification Of THC Prepared By Fractional Distillation Using Flash Column Chromatography

EXAMPLE NO. 8

2.1 g of THC (91% purity) were dissolved in 10 ml isooctane and the solution was transferred onto the top of a silica gel column (30 g silica gel, 40 Mm particle size; dimensions of the column: 2.5 cm×40 cm). The column was eluted with isooctane then a mixture of isooctane-acetone (99:1). Seven fractions were collected and analyzed by GLC. Isooctane-acetone (99:1) fractions containing the bulk of the THC were obtained and yielded 1.84 g of residue (% of THC was 97%).

EXAMPLE NO. 9

1 g of THC (91% purity) was dissolved in 5 ml isooctane and the solution was transferred onto the top of a silica gel column (15 g silica gel, 40 Mm particle size, dimensions: 2.5 cm×40 cm). The column was eluted with isooctane-ethyl acetate mixture in a manner of increasing polarities and the fractions were collected. Fraction No. 5 (eluted with isooctane-ethylacetate 98:2) yielded 0.56 g of residue (% of THC was 97%). Fraction No. 4 (eluted with iso-octane-ethylacetate 98.5:1.5) yields 0.32 g of residue (% of THC was 94.9%).

EXAMPLE NO. 10

1.1 g of THC (91% purity) was dissolved in 5 ml isooctane and the solution was transferred onto the top of a silica gel column (15 g silica gel, 40 Mm particle size, dimensions: 2.5 cm×40 cm). The column was eluted with a mixture of isooctane: isopropyl alcohol in a manner of increasing polarities. Five fractions were collected. Fraction Nos. 4 and 5 (eluted with iso-octane-isopropyl alcohol (98:2 and 95:5, respectively) were combined and yielded 1 g of of THC was 94%).

Purification Of THC By HPLC (Reversed Phase)

EXAMPLE NO. 11

9.6 g of THC (purity 92.8%) was purified on HPLC (Water Delta Prep 4000) connected to Waters 486 Tunable absorbance detector (wave length used: 254 Mm) and using Column Prep Pak C18 (from Waters, Dimensions 46 mm×30 cm, 55–105 Mm, Lot no. T 72852). The eluent was a mixture of methanol: water (75:25). The flow rate was programmed to be 10 ml/minute for 10 minutes, 25 ml/minute for 50 minutes and finally 50 ml/minute for 140 minutes. The results are summarized in the following table:

| Fraction | Time (minutes) | Volume (ml) | Weight (g) | Analysis for THC |
|---|---|---|---|---|
| 1 | 69–96 | 1400 | 0.10 | |
| 2 | 96–105 | 500 | 0.34 | |
| 3 | 105–123 | 1000 | 6.00 | 99% |
| 4 | 123–135 | 600 | 1.98 | 98% |
| 5 | 135–155 | 1000 | 1.00 | 95% |
| 6 | 174–180 | 300 | 0.10 | |

THC can be prepared directly from a hexane extract of *Cannabis sativa* L. by double fractional distillation. The purity of THC by GLC analysis is about 90–92%. Further purification on a silica gel column gives THC with approximately 98% purity.

THC can be prepared directly from a hexane extract of *Cannabis sativa* L. by column chromatography (silica gel) followed by fractional distillation. The purity of THC is about 95–96%. Further purification on a silica gel column gives THC with at least 98% purity.

EXAMPLE NO. 12

5 g of the Cannabis hexane extract (THC content 26.28%; ratio of THC to THCA is 48:52) were heated at 110° C. for 1 hour to convert all the THC acid to free THC, then mixed with 10 g of alumina and 3 mL of hexanes, and the dried slurry was transferred onto the top of alumina column (70 g, basic alumina, 80–225 mesh; dimensions: 3×40 cm). The column was eluted with hexanes then hexanes: mtbe mixtures in a manner of increasing polarities. Results are summarized as follows:

| Fractions | Eluent | Volume | Weight | Comments |
|---|---|---|---|---|
| 1 | Hexanes | 500 mL | 1.60 g | THC content 20.8% |
| 2, 3, 4 | Hexanes:mtbe (98:2) | 1000 mL | 1.05 g | THC content 47.4% |
| 5 | Hexanes: mtbe (90:10) | 1500 mL | 0.90 g | THC content 54.8% |
| 6 | Methanol | 300 mL | 1.00 g | THC content 7.5% |

The column was loaded with 5 g of the extract (THC content 1.35 g). The total weight of the eluted material is 4.55 g (THC content 1.324 g).

This example shows that free $\Delta^9$-THC does not bind strongly to alumina and could easily be eluted with moderately polar solvents.

EXAMPLE NO. 13

20 g of the Cannabis hexane extract (THC content 26.28%, ratio of THC to THCA is 48:52) were heated at 110° C. for 1 hour, then mixed with 40 g of alumina and 10 mL of hexanes and the dried slurry was transferred onto the top of an alumina column (210 g basic alumina, 80–225 mesh; dimensions: 2.9×60 cm). The column was eluted with hexanes, then Hexanes: mtbe mixtures in a manner of increasing polarities. Results are summarized as follows:

| Fractions | Eluent | Volume | Weight | Comments |
|---|---|---|---|---|
| 1 | Hexanes | 450 mL | 1.90 g | THC content 7.1% |
| 2, 3 | Hexanes | 900 mL | 1.54 g | THC content 26.7% |
| 4 | Hexanes | 1000 mL | 1.30 g | THC content 67.6% |
| 5 | Hexanes: mtbe (95:5) | 1000 mL | 4.10 g | THC content 77.8% |
| 6 | Hexanes: mtbe (95:5) | 450 mL | 0.53 g | THC content 63.0% |
| 7 | Methanol | 500 mL | 4.90 g | THC content 12.0% |
| 8 | Methanol | 300 mL | 4.80 g | No THC |

The column was loaded with 20 g of the extract (THC content: 5.26 g). The ratio of the extract to the alumina is 1:12.5. The total weight of the eluted material is 19.07 g (THC content 5.54 g).

This example shows that THCA requires strong polar solvents to elute from alumina.

This example, again, shows the case with which free THC elutes off alumina.

EXAMPLE NO. 14

5 g of the Cannabis hexane extract (THC content 26.28%; the ratio between THC and THCA is 48:52) were mixed with 10 g of activated alumina and 3 mL of hexanes and the dried slurry was chromatographed over an alumina column (70 g, basic alumina, 80–225 mesh, Chrom. Grade; dimensions; 3×40 cm). The column was eluted with hexanes, then hexanes:mtbe mixtures in a manner of increasing polarities and the results are summarized as follows:

| Fractions | Eluent | Volume | Weight | Comments |
|---|---|---|---|---|
| 1, 2 | Hexanes | 900 mL | 1.10 g | No THC |
| 3, 4 | Hexanes:mtbe (98:2) | 400 mL | 0.38 g | THC content 31.6% |
| 5, 6 | Hexanes:mtbe (98:2) | 600 mL | 0.72 g | THC content 81.6% |
| 7, 8 | Hexanes:mtbe (90:10) | 900 mL | 0.25 g | THC content 30.1% |
| 9 | Hexanes: mtbe (50:50) | 500 mL | 0.60 g | THC content 8.6% |
| 10 | Methanol | 200 mL | 0.50 g | THC content 7.6% |

The column was loaded with 5.0 g of the extract (THC content 1.314 g). The total weight of the eluted material is 3.55 g (THC content 0.872 g). This means that 29.0% of the loaded extract is still on the column (0.442 g THC). Further elution of the column with methanol containing 2% acetic acid afforded 0.405 g of THCA.

This example shows that THCA requires strong polar solvents to elute from alumina.

EXAMPLE NO. 15

Extraction

The fine powdered plant material (2.09 kg, THC content: 4.34%; ratio of THC to THC Acids (1:9) was macerated with hexanes (3 gallons) in a 2.5 gallon percolator for 24 hours at room temperature. The hexane extract was collected and the marc was re-extracted with 2 gallons of hexanes for 24 hours. The combined extracts were concentrated at temperature not exceeding 40° C. until the total volume is 3000 ml. Ratio of THC to THC acids: 1:8.6

Column Chromatography

The hexane extract (3000 mL) was transferred onto the top of an alumina column (1.8 kg basic alumina, Lot #

70K3701, Activity grade 1, type WB 2; dimensions: 6×60 cm). The column was eluted with hexanes, then hexanes-acetone mixtures in a manner of increasing polarities. All collected fractions were concentrated at temperature not exceeding 40° C. and analyzed for THC and THC acid content. Results are summarized in the following table:

| Fr. | Eluent | Volume (Liters) | Weight (g) | THC content (GC) | Weight of THC | Ratio of THC to THC acids | Amount of THC (g) | Amount of THCA (g) |
|---|---|---|---|---|---|---|---|---|
| 1, 2, 3 | Hexanes | 9 | 32.0 | 6.3% | 2.00 g | 100:0 | 2.00 | — |
| 4 | Hexanes:acetone (98:2) | 3 | 6.0 | 21.1% | 1.27 g | 100:0 | 1.27 | — |
| 5, 6 | Hexanes:acetone (98:2) | 4 | 25.0 | 22.7% | 5.68 | 100:0 | 5.68 | — |
| 7 | Hexanes:acetone (95:5) | 4 | 13.0 | 23.5% | 3.01 | 100:0 | 3.01 | — |
| 8 | Hexanes:acetone (90:10) | 4 | 8.5 | 20.0% | 1.78 | 87:13 | 1.55 | 0.23 |
| 9 | Methanol* | 4 | 51.4 | 46.3% | 23.83 | 10:90 | 2.38 | 21.45 |
| 10 | Methanol | 4 | 20.0 | 24.1% | 4.82 | 0:100 | — | 4.82 |
| 11 | 3% acetic acid in MeOH** | 4 | | | | | | |
| 12 | 3% acetic acid in MeOH** | 4 | 90.0 | 56.6% | 50.35 | 0:100 | — | 50.35 |

*Fraction # 9 was turbid, filtered to give 1.1 g hydrocarbons (soluble in hexane).
**Fractions # 11 and 12 were combined and the solvent was distilled off at temperature not exceeding 40° C. The residue (150 g) was partitioned between hexanes (2 L) and water (400 mL). The hexane layer was dried over anhydrous $Na_2SO_4$ and distilled to afford 90 g residue.

EXAMPLES NOS. 16–20

Extraction

The fine powdered plant material (2.54 kg, THC content: 4.1%, Ratio of THC to THC acids: 1:13) was macerated with hexanes (2.5 gallons) for 24 hours at room temperature. The hexane extract was collected and the marc was re-extracted with hexanes (1.5 gallons) for 24 hours. The combined hexane extracts were concentrated under reduced pressure at temperature not exceeding 40° C. to 3000 mL. The extract was divided into 8 equal volumes (each volume is 375 mL). Each 375 mL extract equivalent to 317.5 g plant material and contains 13.0 g THC (about 1 g THC and 12 g THC acid).

Adsorbent Used for Column Chromatography
Basic alumina activity grade 1, type WB2;
Neutral alumina, activity grade 1, type WN3

Columns

Column 1: dim. 2.9×60 cm; Column 2: dim. 4.9×40 cm. Each column was packed with 250 g alumina. The height of alumina in column 1 was 37 cm and column 2 was 13 cm.

EXAMPLE NO. 16

375 mL of the concentrated hexanes extract were transferred onto the top of an alumina column (250 g basic alumina, dim: 2.9×60 cm). The column was eluted with hexanes, hexanes: acetone (90:10), methanol, and 3% acetic acid in methanol. Results are summarized as follows:

| Fr. | Eluent | Volume (ml) | Weight (g) | THC content (GC) | Weight of THC | Ratio of THC to THC acids | Amount of THC | Amount of THCA |
|---|---|---|---|---|---|---|---|---|
| 1 | Hexanes | 750 | 3.9 | 3.2% | 0.12 g | 100:0 | 0.12 g | — |
| 2 | Hex:acetone (90:10) | 750 | 4.5 | 12.2% | 0.55 g | 100:0 | 0.55 g | — |
| 3 | Methanol | 250 | 5.0 | 42.0% | 2.10 g | 22:78 | 0.47 g | 1.63 g |
| 4** | 3% $CH_3COOH$/MeOH | 1000 | 14.0 | 62.0% | 8.68 g | 0:100 | — | 8.68 g |

*This is a long column. The height of alumina in it is 37 cm.
**Fr. # 4 was concentrated and the residue was partitioned between hexane (400 mL) and water (200 mL). The hexane layer was separated, dried over anhydrous $Na_2SO_4$ and distilled off.

EXAMPLE NO. 17

375 mL of the concentrated extract were transferred onto the top of alumina column (250 g neutral alumina, Dim: 2.9×60 cm). The column was eluted with hexane, hexane: acetone 95:5, hexane:acetone 90:10, methanol. Results are summarized in the following table:

| fr. | Eluent | Volume (ml) | Weight (g) | THC content (GC) | Weight of THC | Ratio of THC to THC acids | Amount of THC | Amount of THCA |
|---|---|---|---|---|---|---|---|---|
| 1 | Hexanes | 750 | 6.70 g | 9.9% | 0.66 g | 100:0 | 0.66 | — |
| 2 | Hex:acetone (95:5) | 750 | 5.00 g | 22.0% | 1.10 g | 50:50 | 0.55 | 0.55 |
| 3 | Hex:acetone (90:10) | 750 | 2.80 g | 29.7% | 0.83 g | 50:50 | 0.41 | 0.42 |
| 4 | Methanol | 1000 | 8.00 g | 43.3% | 3.46 g | 10:100 | 0.31 | 3.15 |
| 5** | 3% $CH_3COOH$/MeOH | 750 | 8.50 g | 66.5% | 5.66 g | 0:100 | — | 5.66 |

*This is a long column. The height of alumina inside the column is 37 cm.
**Fraction # 5 was purified as in Example 5 by partition between hexane and water.
***It seems easier to elute THC Acids from neutral alumina than basic alumina with 3% acetic acid in methanol.

EXAMPLE NO. 18

350 mL of the concentrated extract was reconstituted to 750 mL with hexane and transferred onto the top of alumina column (250 g neutral alumina, Dim: 2.9×60 cm). The column was eluted with hexane, followed with hexane:acetone 90:10, then 3% acetic acid in methanol. Results are summarized in the following table.

| Fr. | Eluent | Volume (ml) | Weight (g) | THC Content (GC) | Weight Of THC | Ratio of THC to THC acids | Amount of THC | Amount of THCA |
|---|---|---|---|---|---|---|---|---|
| 1 | Hexanes | 800 | 2.0 | 9.8% | 0.20 g | 100:0 | 0.20 | — |
| 2 | Hex:acetone (90:10) | 800 | 5.3 | 20.0% | 1.06 g | 80:20 | 0.82 | 0.24 |
| 3 | 3% $CH_3COOH$/MeOH | 800 | 18.0 | 56.2% | 10.12 g | 5:95 | 0.50 | 9.62 |

*This is a long column, the height of alumina is 37 cm.
**The acetic acid was removed from fraction # 3 by partition between hexane and water.

EXAMPLE NO. 19

325 mL of the concentrated hexanes extract were transferred onto the top of an alumina column (250 g neutral alumina, Dim.: 2.9×60 cm). The column was eluted with hexanes, Hexanes:methyl-t-butyl ether (90:10), Hexanes:mtbe (80:20); then 3% acetic acid in methanol. Results are summarized in the following table:

EXAMPLE NO. 20

650 mL of the concentrated hexanes extract were transferred onto the top of an alumina column (500 g basic alumina, dim.; 4.9×60 cm). The column was eluted with hexanes, hexanes:mtbe (90:10), hexanes:mtbe (80:20), then 3% acetic acid/methanol. Results are summarized in the following table:

| Fr. | Eluent | Volume (Liters) | Weight (g) | THC Content (GC) | Weight Of THC | Ratio to THC to THC acids | Amount of THC | Amount of THCA |
|---|---|---|---|---|---|---|---|---|
| 1 | Hexanes | 1 | 4.1 g | — | — | — | — | — |
| 2 | Hexanes:mtbe (90:10) | 1 | 1.8 g | 17.8% | 0.32 g | 100:0 | 0.32 | — |
| 3 | Hexanes:mtbe (80:20) | 1 | 2.0 g | 21.8% | 0.44 g | 100:0 | 0.44 | — |
| 4 | Hexanes:mtbe (50:50) | 1 | 0.8 g | 20.5% | 0.16 g | 100:0 | 0.16 | — |
| 5 | Methanol | 1 | 5.9 g | 30.9% | 0.82 g | 40:60 | 0.73 | 1.09 |
| 6 | 3% acetic acid/methanol | 2 | 10.7 g | 60.0% | 6.42 g | 0:100 | — | 6.42 |

| Fr. | Eluent | Volume (Liters) | Weight (g) | THC Content (GC) | Weight Of THC | Ratio to THC to THC acids | Amount of THC | Amount of THCA |
|---|---|---|---|---|---|---|---|---|
| 1 | Hexanes | 2 | 7.1 g | — | — | — | — | — |
| 2 | Hexanes:mtbe (90:10) | 2 | 2.2 g | 15.2% | 0.33 | 100:0 | 0.33 | — |
| 3 | Hexanes:mtbe (50:50) | 2 | 4.1 g | 23.3% | 0.96 | 100:0 | 0.96 | — |
| 4 | Methanol | 2 | 18.3 g | 37.6% | 6.88 | 30:70 | 1.16 | 5.72 |
| 5 | 3% acetic acid/methanol | 2 | 18.0 g | 59.0% | 10.62 | 0:100 | — | 10.62 |

*The height of alumina in side the colunm is 26 cm.

EXAMPLE NO. 21

200 g of cannabis plant material (approximately 6% total THC; THC:THCA=1:2.5) was extracted with hexane and the hexane extract was brought to a total volume of 1800 mL. 567 mL of the hexane solution (equivalent to 63 g of plant material) was stirred for two hours with 44 g of basic alumina and filtered. The collected alumina was added to an alumina column containing 19 g fresh basic alumina (dim. 2×22.5 cm, ratio of the extract to alumina is 1:10) and the column was eluted as follows:

| Fr # | Eluent | Volume | Weight | THC/THC acid Ratio |
|---|---|---|---|---|
| 1 | Hexane | 200 mL | — | — |
| 2 | Hexane:MTBE 90:10 | 200 mL | 0.02 g | — |
| 3 | Hexane:MTBE 50:50 | 200 mL | 0.3 g | THC (0.1 g) |
| 4 | Methanol | 400 mL | 1.45 g | THC:THC acid (1:1) (0.23 g each) |
| 5 | 3% Acetic Acid/MeOH | 500 mL | 1.54 g | THC acid (1.0 g) |
| 6 | 3% Acetic acid/MeOH | 500 mL | 0.38 g | THC acid (0.49 g) |

Analysis of the filtrate from the alumina prior to packing showed the presence of THC but no THC acid; that is, by adding alumina to the hexane extract all the THC acid and most of the THC was chelated to alumina. Therefore, simple filtration and washing of the alumina could be used in lieu of a column.

EXAMPLES NOS. 22 AND 23

Fractional distillation of fractions eluted from alumina column with 3% acetic acid in methanol. The content of THC acid in these fractions ranges between 58 to 70%. Bulb to bulb distillation unit was used for the distillation. THC was distilled at temperature between 180–190° C., vacuum: 0.6 mm Hg.

EXAMPLE NO. 22

13.5 g of THC acid fraction (THC acid content 70%) was dissolved in 300 mL of methanol and the precipitate was removed by filtration (0.8 g ppt). The filtrate was distilled off and the residue was divided into two parts: Part A: 6.0 g; Part B: 6.7 g.

Part A was distilled slowly to give:
1. Distillate: 3.7 g, THC content by GC (using internal standard): 82.4%.
2. Remaining in the distilling flask: THC content: 29.5%.

Part B was distilled fast to give:
1. Distillate: 3.0 g, THC content: 81.6%.
2. Remaining in the distilling flask: THC content: 41.9%

EXAMPLE NO. 23

5.0 g of THC acid fraction [THC acid content 58%] was distilled to give:
1. Distillate: 2.8 g, THC content 80.5%.
2. Remaining in the distilling flask: THC content: 32.0%.

EXAMPLE NO. 24

1 g of THC acid fraction [the content of THC acid is 68.4%] was dissolved in 20 mL of methanol. The precipitate that formed was separated by centrifuge (wt 100 mg). The sample was allowed to sit overnight in a refrigerator. The following day further precipitation was observed (40 mg). The sample was filtered using a 0.45 Mm filter. The filtrate was loaded on the HPLC. Solvent System: Methanol: Water (80:20). Equipment: Waters Delta Prep HPLC 4000 with 1000 Prepak module. Column: Prepak C18 cartridge, Waters, 55–105 μm, 125 A; Dimensions: 46 mm×30 cm. THC acid was isolated in >94% purity by HPLC analysis.

EXAMPLE NO. 25

5.8 g of THC acid [THC acid content is 68.4] was dissolved in 20 mL of methanol. The sample was allowed to sit overnight in a refrigerator. The following day the precipitate was filtered. Weight of the precipitate was 0.485 g. The clear filtrate was loaded on the HLPC. Elution was carried out using isocratic solution:methanol:water:acetic acid (80:20:0.01). Again, purified THC acid was isolated from the eluted fractions in solid form.

EXAMPLE NO. 26

Distillation of THCA Acid 4.35 g of THCA fraction (THCA content is 94.1%) was subjected to bulb to bulb distillation. 3.45 g of THC were collected at temperatures between 190–195° C., vacuum 0.50–0.55 mm/Hg. (3.45 g THC corresponds to 3.93 g THCA, therefore, the yield is 90.4%). The purity of the THC collected was >96%.

EXAMPLE NO. 27

A solution of 1 g of marijuana extract that contained 36% of THC and 11% of THC acid in 20 mL of hexane was passed through a column (i.d. 0.5 cm) packed with 5 g of activated acidic aluminum oxide (Aldrich Chemical Company, standard grade, 150 mesh, 58 Å). The column was subsequently eluted with solvent systems including 2.5% acetone in hexane (20 mL), 5% acetone in hexane (20 mL), 10% acetone in hexane (20 mL), methanol (20 mL), and 5% acetic acid in methanol (3×20 mL). Each fraction was collected and analyzed for THC and THC acid content. The amount of THC and THC acid in each fraction were: (1) hexane fraction, 0.003 g of THC; (2) 2.5% acetone in hexane fraction, 0.282 g of THC and 0.005 g of THC acid; (3) 5% acetone in hexane fraction, 0.044 g of THC; (4) 10% acetone in hexane fraction, 0.012 g of THC; (5) methanol fraction, 0.016 g of THC and 0.037 g of THC acid; (6–8) combined 5% acetic acid in methanol fractions, 0.005 g of THC and 0.064 g of THC acid.

EXAMPLE NO. 28

Repeating the work outlined under Example 27 using weakly acidic aluminum oxide gave similar results to those in Example 27.

EXAMPLE NO. 29

An aliquot from a hexane extract of cannabis plant material (THC content 26%) was taken and divided into three samples (A, B, and C).

Sample A 44 mL of methanol was added to 4.4 g of the extract. This was sonicated for at least one hour then refrigerated overnight. The following day the mixture was filtered and the residue was washed with methanol:water (95:5). The residue was dissolved in hexane then dried using a Rotovapor. The filtrate was also dried.

Sample B 41 mL of 90% ethanol/water was added to 4.1 g of the extract. It was sonicated for at least one hour then refrigerated overnight. The following day the mixture was filtered. The residue was dissolved in hexane and dried. The filtrate was also dried.

Sample C 100 mL of ethanol (95%) was added to 10.2 g of the extract. The mixture was sonicated then filtered. The residue was dissolved in hexane then dried. The filtrate was also dried.

All filtrates and residues were then weighed and analyzed. The results are summarized below:

|  |  | SAMPLE A (Methanol) | SAMPLE B (90% Ethanol) | SAMPLE C (95% Ethanol) |
|---|---|---|---|---|
| Weight | Starting Material | 4.4 g | 4.1 g | 10.2 g |
|  | Wt. Filtrate | 1.6 g | 2.0 g | 7.4 g |
|  | Wt. Residue | 3.0 g | 2.0 g | 2.8 g |
| % of THC | Starting Material | 26% | 26% | 26% |
|  | Filtrate | 47.7% | 45.9% | 38.1% |
|  | Residue | 16.9% | 13.9% | 5.7% |
| Amount of THC | Starting Material | 1.28 g | 1.19 g | 2.96 g |
|  | Filtrate | 0.76 g | 0.92 g | 2.82 g |
|  | Residue | 0.50 g | 0.28 g | 0.16 g |
| % Recovery of THC in Filtrate |  | 59.8% | 77.2% | 95% |

EXAMPLE NO. 30

Additional samples from the hexane extract (26% THC) used in Example 1 were used and treated as follows:

Sample D

Add 75.6 mL of ethanol (90%) to the extract (7.56 g). Heat and sonicate until the extract goes into solution. Refrigerate overnight. Filter, then dry residue and filtrate.

Sample E

Add 68.5 mL of ethanol (95%) to the extract (6.85 g). Sonicate until the extract goes into solution then add 1.9 mL of water drop-wise. (Final concentration 92.5%). Refrigerate overnight then filter.

Sample F

Add 75.6 mL of ethanol (200 proof) to the extract (7.56 g). Sonicate until the extract goes into solution. Then add drop-wise 6.1 ml of water. Final ethanol concentration (92.5%). Refrigerate overnight and then filter.

Sample G

Add 73.9 mL of Ethanol (92.5%) to the extract (7.31 g) sonicate until the extract goes into solution then refrigerate overnight. Filter.

The filtrates and residues were then dried, weighed, and analyzed for THC content as follows:

|  |  | SAMPLE D Ethanol (90%) | SAMPLE E Ethanol (95%–92.5%) | SAMPLE F Ethanol (100%–92.5%) | SAMPLE G Ethanol (92.5%) |
|---|---|---|---|---|---|
| Weight | Starting Material | 7.56 g | 6.85 g | 7.56 g | 7.31 g |
|  | Wt. Filtrate | 4.3 g | 4.34 g | 5.07 g | 4.53 g |
|  | Wt. Residue | 3.38 g | 2.37 g | 2.70 g | 2.73 g |
| % of THC | Starting Material | 29% | 29% | 29% | 29% |
|  | Filtrate | 42.2% | 38.3% | 39.5% | 42.8% |
|  | Residue | 11.6% | 7.8% | 10.1% | 16.9% |
| Amount of THC | Starting Material | 2.19 g | 1.99 g | 2.19 g | 2.12 g |
|  | Filtrate | 1.8 g | 1.66 g | 1.92 g | 1.9 g |
|  | Residue | 0.39 g | 0.184 g | 0.27 g | 0.4 g |

-continued

|  |  | SAMPLE D Ethanol (90%) | SAMPLE E Ethanol (95%–92.5%) | SAMPLE F Ethanol (100%–92.5%) | SAMPLE G Ethanol (92.5%) |
|---|---|---|---|---|---|
| % Recovery of THC | Starting Material Filtrate Residue | 82.2% | 83.4% | 87.6% | 89% |

This example shows that the same result is obtained whether the extract is treated directly with the aqueous ethanolic mixture or if it is first dissolved in absolute ethanol followed by the addition of the water to reach a specific alcohol concentration.

EXAMPLE NO. 31

8 g of a hexane extract of cannabis plant material (THC 20.0%) was dissolved in 80 mL of ethanol (200 proof). This solution was divided evenly among four flasks. To each flask water was added to different concentration while stirring. They were filtered and dried and analyzed.

|  |  | FLASK F Ethanol 85% | FLASK G Ethanol 82.5% | FLASK H Ethanol 80% | FLASK I Ethanol 77.5% |
|---|---|---|---|---|---|
| Weight | Starting Material |  |  |  |  |
|  | Wt. Filtrate | 2.16 g | 2.16 g | 2.16 g | 2.16 g |
|  | Wt.Residue | 1.02 g | 0.9 g | 0.8 g | 1.1 g |
| % of THC | Starting Material | 20.0% | 20.0% | 20.0% | 20.0% |
|  | Filtrate | 30% | 37.5% | 33% | 24.2% |
| Amount of THC | Starting Material | 0.4 g | 0.4 g | 0.04 g | 0.4 g |
|  | Filtrate | 0.31 g | 0.38 g | 0.26 g | 0.26 g |
| % Recovery of THC |  | 75% | 84.4% | 66% | 66.5% |

This example shows that 82.5% ethanol gives the highest THC content and the highest overall recovery.

EXAMPLE NO. 32

8 g of a hexane extract of cannabis plant material (THC 20.0%) was dissolved in 80 mL of iso-propanol by sonication. This solution was equally divided into four flasks. To each flask water was added to different concentrations.

|  |  | FLASK 1 IPA 90% | FLASK 2 IPA 80% | FLASK 3 IPA 70% | FLASK 4 IPA 60% |
|---|---|---|---|---|---|
| Weight | Starting Material | 2.0 g | 2.0 g | 2.0 g | 2.0 g |
|  | Wt. Filtrate | 1.60 g | 1.0 g | 0.8 g | 0.8 g |
| % of THC | Starting Material | 20.0% | 20.0% | 20.0% | 20.0% |
|  | Filtrate Residue | 22.5% | 30.4% | 35% | 27% |
| Amount of THC | Starting Material | 0.4 g | 0.4 g | 0.4 g | 0.4 g |
|  | Filtrate Residue | 0.36 g | 0.30 g | 0.28 g | 0.22 g |
| % Recovery of THC |  | 88.7% | 76% | 70% | 54% |

This shows that the highest increase in THC concentration is obtained with 70% iso-propanol.

EXAMPLE NO. 33

17.5 g of cannabis hexane extract (THC content 37%) was dissolved in 100 mL of iso-propanol. This solution was evenly split into seven flasks. To each flask water was added to while stirring to a desired concentration.

|  |  | IPA: Water (77.5%) | IPA: water (75%) | IPA: water (72.5%) | IPA: water (70%) | IPA: water (67.5%) | IPA: water (65%) | IPA: water 7 (62.5% IPA) |
|---|---|---|---|---|---|---|---|---|
| Weight | Starting Material | 2.50 g | 2.50 g | 2.50 g | 2.50 g | 2.50 g | 2.50 g | 2.5 g |
|  | Wt. Filtrate | 1.38 g | 1.39 g | 1.37 g | 1.18 g | 1.05 g | 1.02 g | 0.51 g |
|  | Wt. Residue | 1.60 g | 0.90 g | 1.30 g | 1.39 g | 1.69 g | 1.56 g | 1.6 g |
| % of THC | Starting Material | 37% | 37% | 37% | 37% | 37% | 37% | 37% |
|  | Filtrate | 50% | 47.5% | 57.9% | 48% | 50.9% | 44.7% | 50.7% |
| Amount of THC | Starting Material | 0.925 g | 0.925 g | 0.925 g | 0.925 g | 0.925 g | 0.925 g | 0.925 g |
|  | Filtrate | 0.69 g | 0.66 g | 0.79 g | 0.566 g | 0.534 g | 0.455 g | 0.25 g |
| Recovery of THC | filtrate | 74.5% | 71.3% | 85.4% | 61.2% | 57.3% | 49.2% | 27% |

This example shows that best results are obtained with 72.5% iso-propanol.

EXAMPLE NO. 34

1 g of cannabis hexane extract (THC content 48.8%) was added to each of 7 flasks. To flasks 1–5, 5 mL of acetone was added and sonicated. To each of flasks 6 and 7 add 5 acetonitrile. To flasks 1–5 water was added while stirring. Flask 6 was filtered as is. To flask 7, 1 mL of hexane was added, then 2 mL of acetonitrile. This was filtered then the filtrate was concentrated to remove the hexane. It was filtered again.

| Flask # | 5 mL of Solvent | Volume of H20 | % Solvent | Weight of Filtrate | Weight of Residue | Amt. THC in Filtrate | Amt. THC in Residue | % Recovery |
|---|---|---|---|---|---|---|---|---|
| 1 | Acetone | 0.1 mL | 98% | 735 mg | 248 mg | 49.8% | 41% | 75% |
| 2 | Acetone | 0.2 mL | 96% | 704 mg | 302 mg | 52.4% | 38.5% | 75.6% |
| 3 | Acetone | 0.5 mL | 90% | 866 mg | 153 mg | 42.7% | 33% | 75.8% |
| 4 | Acetone | 1.0 mL | 83% | 583 mg | 346 mg | 48.8% | 42.1% | 58.3% |
| 5 | Acetone | 0 mL | 100% | 924 mg | 95 mg | 49.4% | 23.3% | 93% |
| 6 | acetonitrile | 0 mL | 100% | 585 mg | 417 mg | 59.6% | 32% | 71% |
| 7 | acetonitrile (with hexane at a ratio of 7:1) | 0 mL | 100% | 676 mg | 324 mg | 54.5% | 25.9% | 75.5% |

EXAMPLE NO. 35

10 g samples of a hexane extract of cannabis plant material (26% THC) were dissolved in the following solvents. Acetonitrile (95 mL, 80 mL, and 70 mL), iso-propanol (70 mL), and methanol (100 mL). Different volumes of water were then added to each solution to yield five final solutions of the extract in 95% acetonitrile, 80% acetonitrile, 70% acetonitrile, 70% iso-propanol, and 100% methanol. These final solutions were then filtered and both were dried, weighed, and analyzed for THC content. The results are shown below:

| Solvent | Weight of Filtrate | Weight of Residue | Amt, THC in Filtrate | Amt THC in Residue | % Recovery |
|---|---|---|---|---|---|
| Acetonitrile (80%) | 5.19 g | 4.73 g | 40.1% (2.08 g) | 15.8% (0.75 g) | 73.8% |
| Acetonitrile (70%) | 3.44 g | 7.23 g | 31.6% (1.09 g) | 19.5% (1.4 g) | 38.5% |
| Acetonitrile 95%) | 6.37 g | 3.04 g | 35.8% (2.28 g) | 11.0% (0.33 g) | 80.8% |
| Iso-propanol (70%) | 5.72 g | 3.91 g | 34.3% (1.96 g) | 18.5% (0.72 g) | 68.5% |
| Methanol (100%) | 8.21 g | 1.64 g | 29.7% (2.47 g) | 10.6% (0.17 g) | 87.5% |

The results show that 80% or 95% acetonitrile produces comparable results to the 70% iso-propanol.

EXAMPLE NO. 36

Partitioning of Crude Hexane Extracts with Acetonitrile or Acetonitrile Water Mixtures 10 mL aliquots of a hexane solution of cannabis extract (THC content 37%) containing approximately 1.8 g extract were partitioned with 10 mL of either acetonitrile, acetonitrile: water (9:1) or acetonitrile:water (8:2). The acetonitrile layer was separated and the partitioning in each case was repeated two more times with 10 mL each of the same solvent. The combined acetonitrile fractions as well as the hexane fraction were analyzed for THC content.

| Fractions | Weight | % of THC |
|---|---|---|
| 100% Acetonitrile | | |
| acetonitrile fraction | 1.15 g | 64.5% |
| hexane fraction | 0.60 g | 7.3% |
| 90% Acetonitrile: | | |
| acetonitrile fraction | 1.02 g | 69.3% |
| hexane fraction | 0.84 g | 10.7% |
| 80% Acetonitrile | | |
| acetonitrile fraction | 0.84 g | 57.6% |
| hexane fraction | 1.13 g | 20.7% |

This example shows that in all cases the THC concentrates in the acetonitrile layer with 90% acetonitrile giving the highest increase in THC concentration

EXAMPLES NOS. 36–38

Partitioning of crude cannabis extracts with methanolic KOH solutions:

EXAMPLE NO. 36

10.9 g of the crude heptane extract (THC content 32.05%) was dissolved in 100 mL of hexane and shaken twice with 40 mL of 1 N KOH in MeOH-H$_2$O (90:10). The hexane layer was collected, dried (2.2 g), and analyzed for THC content (2.2%). The methanolic KOH layer was acidified by adding 65 mL of 2 N HCl, then extracted by shaking twice with hexane (200 mL). The hexane layer was collected, dried (7.2 g) and analyzed for THC (49.1%) with >95% recovery.

EXAMPLE NO. 37

10.1 g of the crude heptane extract (THC content 32.05%) was dissolved in 100 mL of hexane and shaken twice with 40 mL of 1 N KOH in MeOH-H$_2$O (80:20). The hexane layer was collected, dried (3.4 g), and analyzed for THC content (4.4%). The methanolic KOH layer was acidified by adding 65 mL of 2 N HCl, then extracted by shaking twice with hexane (200 mL). The hexane layer was collected, dried (5.7 g), and analyzed for THC content (54.05%) with a 95% recovery.

EXAMPLE NO. 39

33.0 g of the crude heptane extract (THC content: 41.4%) was dissolved in 300 mL of hexane and shaken twice with 120 mL of 1 N KOH in MeOH-H$_2$O (70:30). The hexane layer was collected, dried (8.5 g) and analyzed for THC content (7.9%). The methanolic KOH layer was acidified by adding 200 mL of 2 N HCl, then extracted by shaking twice with hexane (600 mL). The hexane layer was collected, dried (21.1 g) and analyzed for THC content (62.5%), with >95% recovery.

EXAMPLE NO. 40

Direct Treatment of Cannabis Extracts with Methanolic KOH Solution 5.28 g of the heptane extract (THC content 41.4%) was sonicated very well with 50 mL of 0.25 N KOH in methanol and filtered. The precipitate weighed 1 g (most probably hydrocarbons). The filtrate was acidified with 15 mL of 1 N HCl and extracted twice with hexane (100 mL×2) to give 3.18 g residue (THC content 70.02%), with almost quatitative recovery.

EXAMPLE NO. 40

Reprocessing of the Residue Left After Fractional Distillation of Cannabis Extracts 34 g of marijuana extract containing 55% of THC was distilled under vacuum (0.3 mmHg) and the distillate at 174–192° C. was collected to give 17.8 g of pale yellow oil that contained 82% THC.

The residue remaining in the distillation flask was cooled to room temperature and weighed 15.7 g which analyzed for 25% THC. This was triturated with 50 mL of methanol and filtered. The filter cake was triturated with another 50 mL of methanol and filtered. The filtrates were combined and evaporated to give 7.04 g of oil which analyzed for 55% THC (98% recovery).

References

1. ElSohly, M. A.; Harland, E.; and Waller, C. W.; Cannabinoids in glaucoma II: The effect of different cannabinoids on the intraocular pressure of the rabbit; *Curr. Eye Res.;* 3(6):841–850, 1984.
2. El-Mallakh, R. S.; Marihuana and migraine, *Headache,* 27(3):442–443, 1987.
3. Volfe, Z.; Dvilansky, I. A., and Nathan, I.; Cannabinoids block release of serotonin from platelets induced by plasma from migraine patients; *Int. J. Clin Pharmacol. Res.,* 5(4):243–246, 1985.
4. Maurer, M; Henn, V.; Dirtrich, A.; and Hofmann, A.; Delta-9-tetrahydrocannabinol shows antispastic and analgesic effects in a single case double-blind trial; *Eur. Arch. Psychiatry Clin. Neurosci.,* 240(1):1–4, 1990.
5. McLendon, D. M., Harris, R. T.; Maule, W. F.; Suppression of the cardiac conditioned response by delta-9-tetrahydrocannabinol: A comparison with other drugs; *Psychopharmacology,* 50(2):159–163, 1976.
6. ElSohly, M. A., Stanford, D. F.; Harland, E. C.; Hikal, A. H.; Walker, L. A.; Little, T. L., Jr.; Rider, J. N.; and Jones, A. B.; Rectal bioavailability of delta-9-tetrahydrocannabinol from the hemisuccinate ester in monkeys; *J. Pharm. Sci.,* 80(10):942–945, 1991.
7. ElSohly, M. A., Little, T. L., Jr.; Hikal, A.; Harland, E.; Stanford, D. F.; and Walker L. A.; Rectal bioavailability of delta-9-tetrahydrocannabinol from various esters; *Pharmacol., Biochem., Behav.,* 40:497–502, 1991.
8. Mattes, R. D.; Shaw, L. M.; Edling-Owens, J., Engleman, K.; and ElSohly, M. A.; Bypassing the first-pass effect for the therapeutic use of cannabinoids; *Pharm., Biochem., Behav.,* 44(3):745–747, 1991.
9. Mattes, R. D.; Engelman, K.; Shaw, L. M.; and ElSohly, M. A.; Bypassing the first-pass effect for the therapeutic use of cannabinoids, *Pharmacol., Biochem., Behav.,* 49(1):187–195, 1994.
10. Brenneisen, R.; Egli, A.; ElSohly, M. A.; Henn, V.; and Speiss, Y.; the effect of orally and rectally administered delta-9-tetrahydrocannabinol on spasticity: A pilot study with 2 patients; *Inter. J Clin. Pharmacol. and Therapeutics,* 34(10):446–452, 1996.
11. Wollner, H. J.; Matchett, J. R.; Levine, J.; and Loewe, S.; Isolation of a physiologically active tetrahydrocannabinol from *Cannabis sativa resin; J. Am. Chem. Soc.,* 64:26–29, 1942.
12. DeRopp, R. S.; Chromatographic separation of the phenolic compounds of *Cannabis sativa; J. Am. Pharmacol. Assoc., Sci. Ed.,* 49:756, 1960.
13. Gaoni, Y.; and Mechoulan, R.; Isolation, structure, and partial synthesis of an active constituent of hashish; *J. Am. Chem. Soc.,* 86:1646–1647, 1964.
14. Korte, F.; Sieper, H.; and Tira, S.; New results on hashish-specific constituents; *Bull. Narcotics,* 17:35–43, 1965.
15. Mechoulam, R.; and Gaoni, Y.; Recent advances in chemistry of hashish; *Fortschr. Chem. Org. NatStoffe,* 25:175–213, 1967.
16. Verwey, A. M. A.; and Witte, A. H.; A rapid method of preparation of THC by Isolation of THCA from hashish; *Pharm. Weekblad,* 107:415–416, 1972.

We claim:

1. In a method for the isolation of delta-9-tetrahydrocannibinol (THC) from Cannabis plant material, the improvement wherein delta-9-THC Acid and THC are separately obtained comprising the steps of:

(a) extracting the Cannabis plant material to obtain extracts rich in the acid;

(b) chelating delta-9-THC acid in cannabis extracts rich in the acid on alumina;

(c) eluting from the alumina non-acid components of the extract chelated on alumina with organic solvents; and (d) eluting the delta-9-THC acid with strong polar solvents.

2. The process of claim 1 wherein the alumina is selected from basic, neutral, or acidic types of alumina.

3. The process of claim 2 wherein an organic solvent is used to apply the extract to alumina which is a hydrocarbon solvent such as a hexane, heptane or iso-octane either alone or in admixture with low concentrations of polar solvents and/or ethers.

4. The process of claim 3 wherein the solvents used to wash the non-acid components comprise a mixture of hydrocarbon solvent with increasing concentration of a polar solvent, such as acetone, ethylacetate, ether, and methyl-t-butyl ether and increasing the polarity of the eluting solvent all the way to methanol.

5. The process of claim 4 wherein the solvent used to elute the delta-9-THC acid from the alumina comprises a mixture of methanol and a strong acid modifier such as acetic acid with the latter representing 1–10% of the mixture.

* * * * *